(12) United States Patent
Saini et al.

(10) Patent No.: US 6,717,658 B1
(45) Date of Patent: Apr. 6, 2004

(54) DETECTION OF LIQUIDS

(75) Inventors: Selwayan Saini, Millbrook (GB); Lawrence Ritchie, Milton Keynes (GB); Clive Patrick Ferguson, Welling (GB)

(73) Assignees: Cranfield University, Cranfield (GB); The National Grid Company PLC, Leatherhead (GB)

( * ) Notice: Subject to any disclaimer, the term of this patent is extended or adjusted under 35 U.S.C. 154(b) by 0 days.

(21) Appl. No.: 09/926,220
(22) PCT Filed: Mar. 27, 2000
(86) PCT No.: PCT/GB00/01161
§ 371 (c)(1),
(2), (4) Date: Oct. 17, 2001
(87) PCT Pub. No.: WO00/58714
PCT Pub. Date: Oct. 5, 2000

(30) Foreign Application Priority Data

Mar. 26, 1999 (GB) ............................................. 9906949

(51) Int. Cl.$^7$ .................................................. G01N 33/28
(52) U.S. Cl. ............................................................ 356/70
(58) Field of Search .................... 356/70, 436–440, 356/246

(56) References Cited

U.S. PATENT DOCUMENTS

| | | | |
|---|---|---|---|
| 4,159,420 A | 6/1979 | Tsunoda | |
| 4,609,821 A | 9/1986 | Summers | |
| 5,831,743 A | 11/1998 | Ramos et al. | |

FOREIGN PATENT DOCUMENTS

| | | |
|---|---|---|
| EP | 0 282 009 | 9/1988 |
| EP | 0 505 581 | 9/1992 |
| EP | 0 598 341 | 5/1994 |
| GB | 2 234 061 | 1/1991 |

*Primary Examiner*—Frank G. Font
*Assistant Examiner*—Amanda H. Merlino
(74) *Attorney, Agent, or Firm*—Oblon, Spivak, McClelland, Maier & Neustadt, P.C.

(57) ABSTRACT

Liquid, particularly leaked oil or other hydrophobic liquid, is detected by a sensor. This preferably has a hydrophobic membrane (G) that takes up the oil selectively, a radiation source (A) that beams radiation at an interface between the membrane (G) and a window (F), and a radiation detector (H) that receives radiation resulting from interaction (such as reflection, scattering or fluorescence) of the input radiation with the liquid-containing membrane (G). The detector may employ a spectrofluorimeter (H) whose output can be used to characterise the liquid.

14 Claims, 7 Drawing Sheets

DETECTION OF LIQUIDS

TECHNICAL FIELD

The present invention relates to a method and apparatus for use in the detection of liquids, particularly hydrophobic liquids such as oils. It may be used for monitoring for leakage. A preferred type of embodiment employs an optical method that is capable of detecting and preferably identifying hydrocarbon liquids such as mineral or synthetic oils, petroleum, diesel, insulating oils etc. emanating from a leaking vessel, container or storage device.

A number of vessels are routinely used to carry or hold hydrocarbon solvents such as oils in a wide variety of applications. Examples include oil filled underground power cables, underground petroleum storage tanks, above surface oil containers for industrial or domestic heating, oil filled power transformers and equipment etc. Release of the container's contents, deliberate or accidental or via corrosion over time will have economic and environmental consequences. The routine monitoring of the release of oil/solvents from these containers can be an arduous task because of the myriad of locations, distribution and varieties of such devices. A more convenient method would be one where a sensor device is placed at each container location and was able to perform continues or periodic monitoring as required. Ideally, the sensor should be able to detect any oil/solvent spillage as soon as it occurs in order that remedial actions can be made to minimise any ongoing loss into the environment. Such a device is referred to here as an in-situ sensor or monitor. Ideally, a remotely controlled sensor device that could automatically warn of oil/solvent leakage is preferred especially where container vessels or locations are difficult to access, are widely distributed or where checks for leakage are made infrequently. Examples of such situations are discussed below.

Oil Filled Underground Power Cables

The continual supply of electrical power throughout a country relies on the integrity of underground and overhead power cables. Ease of maintenance requires that most power cables are run above ground, but where this is not possible, such as in cities, the power lines are buried some meters underground. At the operating voltages of 132 kV and above, many of the cables in service are of the oil filled type. Oil-filled cables are normally laid in sections of between 200–400 meters, which are then joined together in specially constructed joint bays. The cables and joints are then encased in a special backfill material such as speciality grade sands or cement-bound-sand (CBS).

Voids in the cable insulation can result in partial discharge activity and ultimately electrical breakdown of the cable. In an oil filled cable the oil, if maintained under sufficient pressure, prevents the formation of gaseous voids. The hydraulic system is designed to be maintained at a positive pressure at the highest points on the route profile and for this maximum static pressure at the lower points on the profile can be up to 5.25 bar.

Problems arise with this type of cable when leaks appear in the pressure retaining metal jacket. Where there is a leak, the cable must be switched out if adequate pressure cannot be maintained in order to prevent the risk of electrical breakdown of the cable. The oil used in new cable installations is a synthetic mixture of alkylated benzenes, with the greatest component being dodecylbenzene (DDB). (Older cable installations employ mineral oil for insulation, but this is gradually being phased out.) Although it has not been shown to be directly carcinogenic to humans, it is of a class of chemicals (substituted benzenes) some of whom do have toxic properties, so there are environmental implications associated with leakage of this oil.

Due to the nature of the cable, leaks most often occur where two cable ends are joined, in specially constructed joint bays. Leaks in the body of the cable are much rarer, and are usually only caused by the over-zealous use of earth digging machinery, and so are usually located immediately. Nevertheless, should a leak occur it would be detected by a fall in operating pressure over a period of time. Then the problem lies in locating in which of the many joint bays along the length of the cable the leak has sprung. Prior to this invention, detection relied on hydraulic bridge techniques, which are both time consuming and unreliable. A much-preferred method would be to install in each joint bay a device capable of providing immediate notification of a leak condition and thus ensure swift remedial measures, avoid the risk of excavating a healthy bay and minimise any disruption to power supplies.

Underground Petrol Tanks

The burial of tanks containing hydrocarbon liquids has been a method of storage around the world. One of the main reasons that this method is employed is for the reduction in the risk of fire and explosion that is afforded. When sited underground the tank is protected from damage by the myriad of possible causes, and will also save on space. However, placing tanks under the ground has its own hazards. The particular problem with underground tank storage is one of tank corrosion. Whereas above ground tanks are easily inspected, underground tanks by the nature of their position are a more difficult monitoring challenge. The stability of the soil is not easily assessed, any leaks that may be occurring may continue for months or even years, and even a small leak of one drop per second may result in a loss to the soil of 400 liters per annum. Awareness of the problems has been increasing; in Britain, particularly with the Environmental Protection Act of 1990 and the Environment Act of 1995 emphasising the polluter pays principle, and increased concern over water supplies. In the USA, awareness and concern are particularly high, especially in some areas where dependence on groundwater is high. The Environmental Protection Agency estimates that 41,600,000 liters of petrol alone may be leaking from underground storage tanks every year.

A preferred route to monitoring possible leaks from underground tanks would be to install an in-situ sensor device that was buried near the tank and capable of sensing whether or not a leak had occurred, thus allowing the user to determine the integrity of the vessel on a continuous basis.

IN-SITU MONITORING DEVICES—PRIOR ART

One design for such a sensor (TraceTek from Raychem, USA) (see http://www.raychem.com/products/chemelex/technolocy.htm for details.) involves the two poles of an electrical switch being separated by a degradable polymer. Not only is this system expensive and difficult to install it can also produce false indications where there are low level background traces of oil, as this tends to degrade the polymer over extended periods of time.

Other methods of leak detection involve hydraulic bridge techniques. This system requires very small pressure differences to be measured and these measurements can be difficult where there are transient pressure variations and/or where cable records are unreliable and/or where there are localised thermal conditions owing for example to another heat source.

DISCLOSURE OF INVENTION

According to the present invention in a first aspect there is provided a method of monitoring for the presence of liquid at a site comprising: locating at said site a sensor assembly comprising a radiation source and a radiation detector and/or analyser arranged to detect and/or analyse radiation which results from the emission of radiation by the source; causing the radiation source to irradiate a sensing location; and employing said detector/analyser to receive radiation, the arrangement being such that the nature and/or amount of radiation received by the detector/analyser is affected by the presence of liquid at the sensing location. The liquid may be a hydrophobic liquid such as oil. The sensor assembly may include a hydrophobic membrane or other element which preferentially takes up hydrophobic liquid. This affects its optical properties, e.g. reflectance of light at a membrane/glass interface. The element may be or include a fluorocarbon, e.g. polyvinylidene fluoride.

Radiation from the source interacts with the liquid in the sensing location, e.g. by one or more of reflection, absorption, transmission, scattering and fluorescence. Radiation resulting from the interaction is detected and/or analysed by the detector/analyser.

In a second aspect the invention provides an assembly comprising a vessel containing a liquid and a sensor assembly located at a site potentially contaminated by liquid leaking from the vessel and adapted to carry out the method as defined above.

In a third aspect the invention provides a sensor assembly for use in monitoring for the presence of hydrophobic liquid at a site, said assembly comprising: a hydrophobic element which is disposed so that in use it is exposed to the environment at the site and which is adapted to take up hydrophobic liquid; a radiation source arranged to irradiate at least a portion of the hydrophobic element; and a radiation detector and/or analyser arranged to receive radiation resulting from the interaction of the source's radiation with the hydrophobic element.

In a preferred type of embodiment the invention provides an in-situ device for the detection and identification of oil or other hydrocarbon products that have leaked from vessels such as underground power cables or petrol storage tanks.

Detection of oil may be achieved by measuring the intensity of light reflected or emitted from a hydrophobic membrane at an optical window in contact with the external environment, when oil is present in the environment, it is absorbed into the hydrophobic membrane causing a change in the intensity of the reflected beam. The membrane can be one from the fluorocarbon range of membrane materials such as polyvinylidene fluoride. Identification of the oil is provided by measuring the spectral properties of the reflected beam or the spectral properties of light emanating from oil absorbed in the membrane.

In a preferred embodiment, the sensor has been designed for specific application to detecting oil leakage from underground power cables although it has clear application in other situations where oil or other hydrocarbons may leak from a vessel located underground, above ground or in water.

There may be a plurality of sensors for installation at different locations around a potential source of liquid. They may be connected via waveguides (such as fiber optics) to a detector/analyser. There may be a "multiplexing unit" such that the detector/analyser is connectable to one sensor at a time, the connected sensor being selectable and/or determined by programmed switching.

The invention can be left to operate in-situ at the monitoring site enabling convenient continuous or periodic monitoring of the environment. Using telecommunications methods known to those skilled in the art, it is possible to transfer data from the monitoring site to a remote destination. The invention has several applications where monitoring oil or hydrocarbon leaks is required or preferred. Examples are shown in the technical description.

In the preferred embodiment, the device can be buried in sand or soil or immersed in water that surrounds an oil carrying vessel or container. If oil leaks from the vessel and contacts the sensor, it will be detected as a change in signal intensity or spectral characteristics. Such a system can therefore be used as an in-situ monitoring device that is triggered when a leak has occurred.

MODES FOR CARRYING OUT THE INVENTION

1. Development of Sensor Device for Monitoring Cable Oil Leaks

One of the simplest optical measurement techniques was chosen for the sensor: the measurement of the intensity of the beam reflected from a sand surface adjacent a window. One or a number of wavelengths of light could be monitored. The presence of oil in the sand directly against a glass sensing window should cause a significant drop in the beam's reflected intensity due to absorption by the oil and diffraction occurring at the glass/oil interface. Interference in the optical signal would be caused mainly by the presence of water in the surrounding medium (which may be cement bound sand (CBS)), which to some extent would mimic the properties of oil in the, sand.

Initial investigations of the optical properties of known mixtures of sand, water and cable oil were performed using an Instruments SA Fluoromax II spectrofluorimeter operating in front-face collection mode, with the sample contained within methacrylate UV fluorimetry cuvettes, the total reflectance of each of the standard mixtures was measured for different excitation wavelengths.

Five prototype sensors were built in-house for sensor characterisation. Solid state components were selected for their longevity, reliability and very low power consumption.

Figure 1:
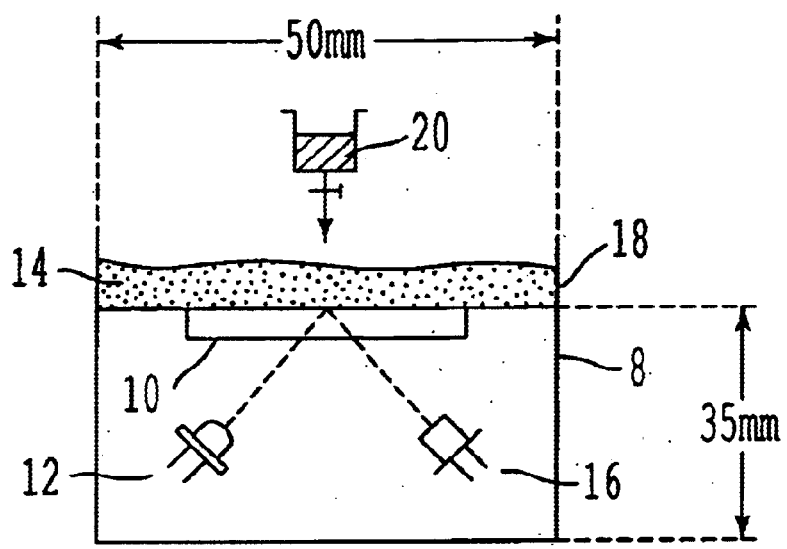
FIG. 1 is a schematic view of apparatus used to test prototype transducers.

The apparatus is shown in FIG. 1. Its design was selected for its simplicity and ease of testing. It has a housing 8, one side of which has a glass window 10. Within the housing there is a near-IR photodiode source 12 which illuminates a surface of the window 10, which forms the sensing area of the module to be brought into contact with the sand samples 14, contained in a Petri dish 18. Light reflected from the sample window 10 is detected and measured using a near-IR phototransistor 16, also mounted in the housing. Controlled amounts of oil can be added (20) to the sand 14.

Figure 2:
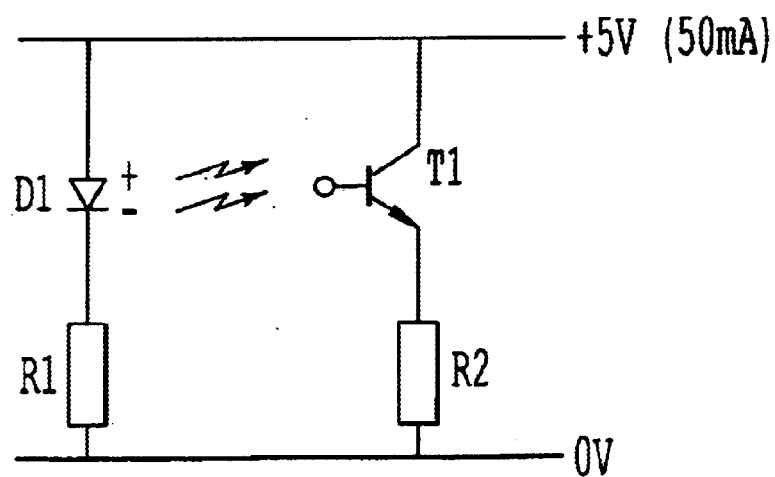
FIG. 2 is a circuit diagram of a prototype reflectance measurement circuit as used with the apparatus of FIG. 1.

The schematic for the reflectance measurement electronics is shown in FIG. 2. A photodiode D1 (e.g. SFH 409) and a first resistor R1 (e.g. 100 ohm) are in parallel with a phototransistor T1 (e.g. SD 3443) and a second resistor R2 (e.g. 1 k.ohm), across a DC voltage (e.g. 5 v). Current through the phototransistor, T1, is dependent on the flux of light illuminating the transistor's base electrode. The limiting resistor, R2, converts the current to an output voltage between zero and five volts.

Infrared components were chosen so that stray light would not interfere with the results (this was particularly important for tests carried out in the laboratory), and for optimum sensitivity as silicon operates most efficiently in the near IR. For simplicity, no filters were used and the total LED output was used as the excitation signal. Other sources giving rise to other wavelengths could also be used if required for a particular application. Absorption of such wavelengths could be used for the sensing mechanism especially where spectroscopic measurements (source emission or detection over a series of wavelengths) are being made. Alternatively, the fluorescence or Raman characteristics of the oil could also be measured using an alternative optical set-up. The photodiode, D1, and phototransistor, T1, were chosen for their similarities in spectral output and response.

In a further embodiment of the sensor, light from the source could be channelled along a fiber optic tube or planar waveguide. In this case, the returned light would be modified in the presence of oil. The fiber optic design is particularly relevant when distributed sensing is required as a number of fibres could be multiplexed to one sensor to cover a larger sampling area.

1.1 Verification of the Prototype Transducer

To represent the CBS that surrounds the underground cables, test samples were made by mixing dried soft building sand with water. Water is most often present in the CBS between 0% and 10% by mass. Saturation, which prevents oil from entering the sand, was found to occur for water contents approaching 30% so a maximum of 20% water was used during testing. The sand and water mixture (totalling approximately 20 g) was then placed inside a plastic petri-dish which was placed upon the glass window of the sensor (as in FIG. 1). Cable oil was then added dropwise to the sand mixture to simulate oil from a leaking cable encroaching upon the active sensing region. This arrangement was chosen as it permits rapid evaluation of the sensor (the oil is drawn towards the sensing window by gravity and capillary action) and it requires a minimal amount of sand and oil, so results in a minimum of waste material.

Figure 3:
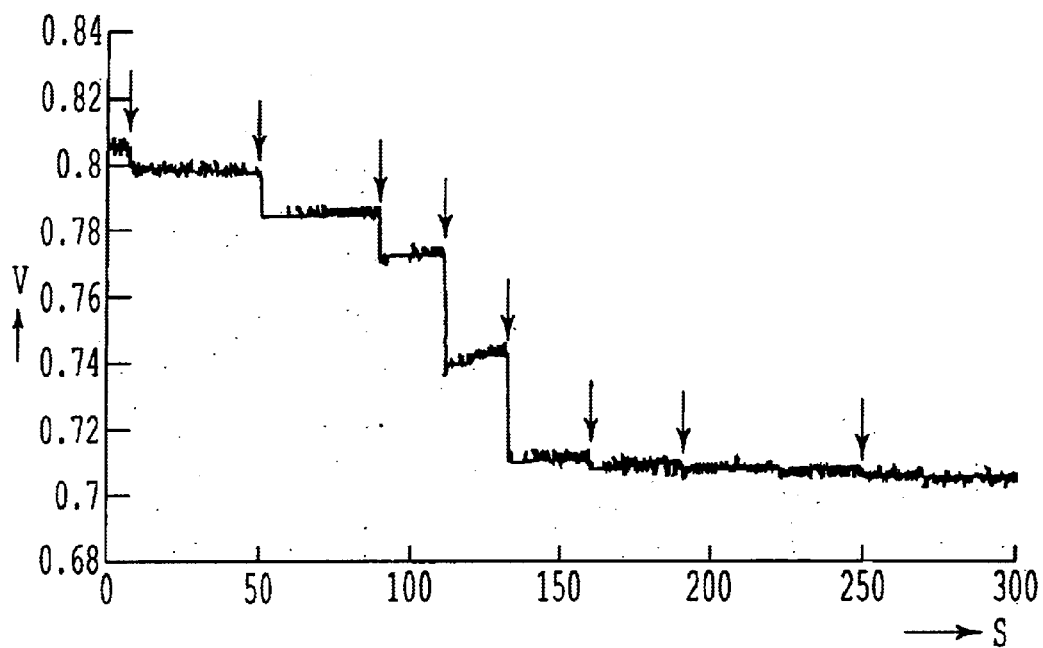
FIGS. 3–6 are graphs of reflectance voltage (V) against time(s) showing responses of the prototype transducer.

The response of the transducer to oil additions is shown in FIG. 3. Oil was added to sand containing 10% water (by weight). Each arrow represents addition of 1% by weight of oil. There is clearly a drop in reflectance proportional to the amount of oil added, raising the possibility of a quantitative oil sensor. It is interesting to note the rapid sensor response time observed in the figure. It takes less than five seconds for the reflectance voltage to stabilise at a new value after oil addition.

Figure 4:
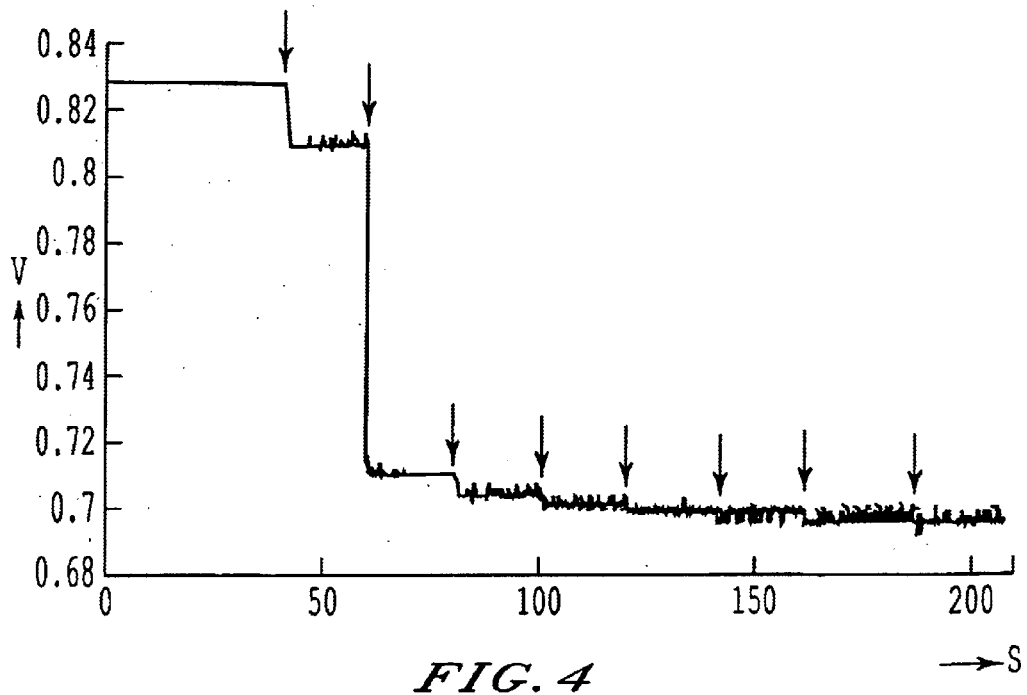

Because water content in the sand may exhibit wide variations, it was important to determine the extent to which this may interfere with oil measurement. Unfortunately, it was found to have a very considerable effect. FIG. 4 shows the sensor output voltage (which is proportional to reflectance) as water is added to sand. Initially the sand contained 10% water and each arrow represents addition of 1% by weight of water. The response to water is similar to that for oil shown in FIG. 3, effectively prohibiting the use of this method for oil detection when water content may also vary, as there is no way to differentiate between water and oil at the sensing window. Monitoring rate of change instead of absolute reflectance could be used to detect a flood of oil, since this would give a sudden change in response whereas the passage of water through the sand would be more gradual. However, we decided to develop a physical solution to the problem.

1.2 Improvement in Selectivity and Sensitivity: Use of Oil-Selective Membrane

To remove the problem of water interference, a Fluorotrans membrane (polyvinylidene fluoride) was introduced between the sand and the sensing window. (It was placed in the petri dish 18 before the sand 14 was added.) This membrane is extremely hydrophobic, repelling water from the sensing surface while attracting organic fluids such as oil. In addition to increasing selectivity, this also increased sensitivity, as the change in reflectance of the membrane as it absorbs oil is considerably larger than that directly observed in sand.

Figure 5:
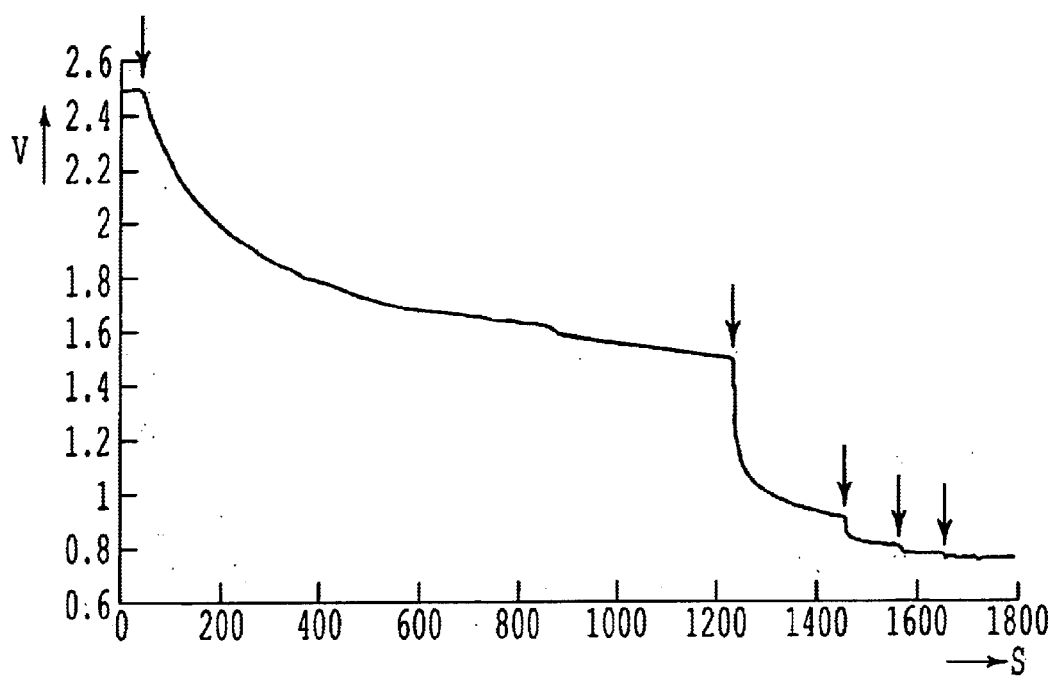
Figure 6:
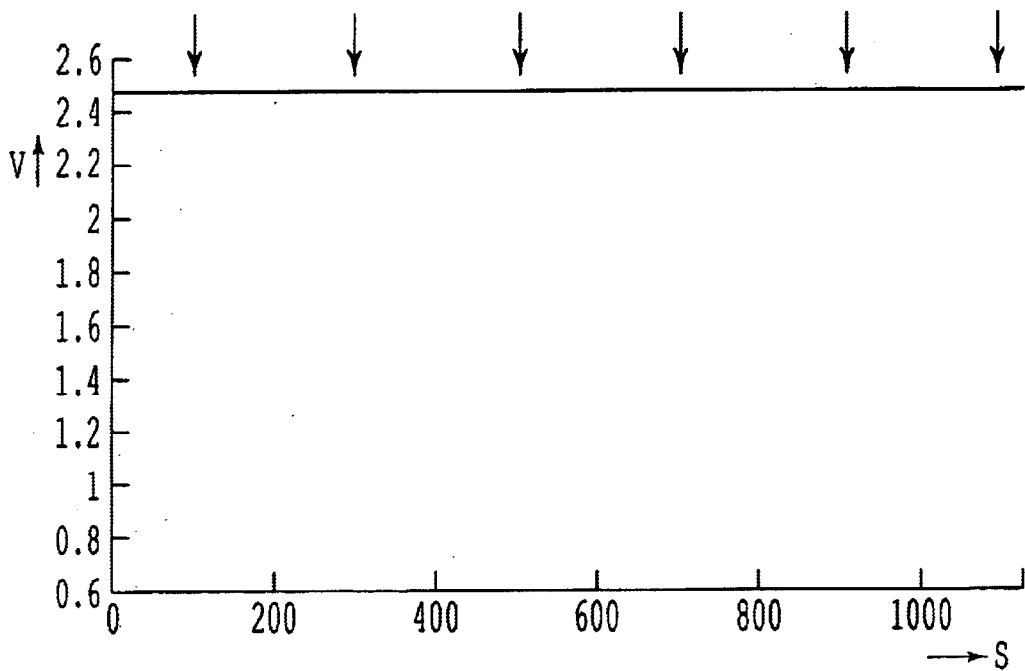

FIG. 5 shows the response obtained of the membrane-covered sensor when oil was added to the sand, each arrow indicating a 1% increase in oil concentration. The response time is significantly increased for low concentrations with respect to that achieved without the membrane, but the latency is still small with respect to the 24 hour sampling period anticipated. FIG. 6 shows how insensitive the sensor response is to changes in water concentration, each arrow representing a 1% increase in water concentration.

1.3 Construction of Prototype

Figure 8:
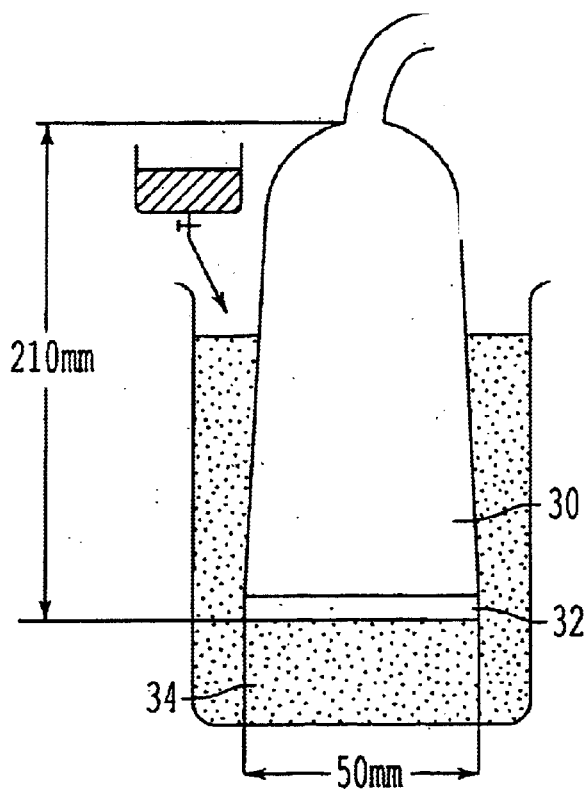
FIG. 8 is a schematic view of apparatus used to evaluate a sensor.

Having proved the concept of the oil detection method, the method was embodied into a manufacturable sensor suitable for long term operation underground. A tube like design was used that incorporated the sensor at one end (termed the sensor head) (FIG. 8). The sensor head 30 comprises the oil detecting assembly, consisting of the reflectance measurement circuit, a glass window, a disc of Fluorotrans membrane and a removable glass retaining ring 32 used to keep the glass and membrane discs in place.

Figure 7:
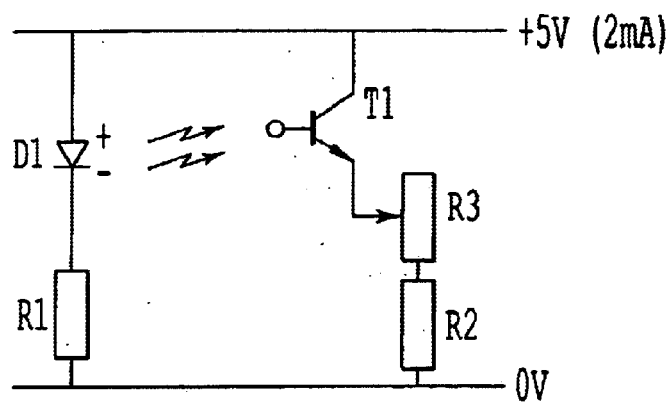
FIG. 7 is a view like FIG. 2 showing a modified circuit diagram.

The reflectance measurement circuit used in this device is shown in FIG. 7. This is generally as shown in FIG. 2 and described above, except that (i) the current requirement of the circuit was reduced from 50 mA to 2 mA by altering the value of resistor R1 to 2 k.ohm (this results in a difference in reflectance voltage with respect to that provided by the prototype sensors); and (ii) a trimmer R3 was added in series with R1 to enable the sensitivity of the transducer to be adjusted to account for any manufacturing-induced variations in the performance of the photodiode and phototransistor. The revised circuit is shown in FIG. 7. The trimmer R3 may be a 100 k.ohm multi-turn cermet trimmer.

Figure 9:
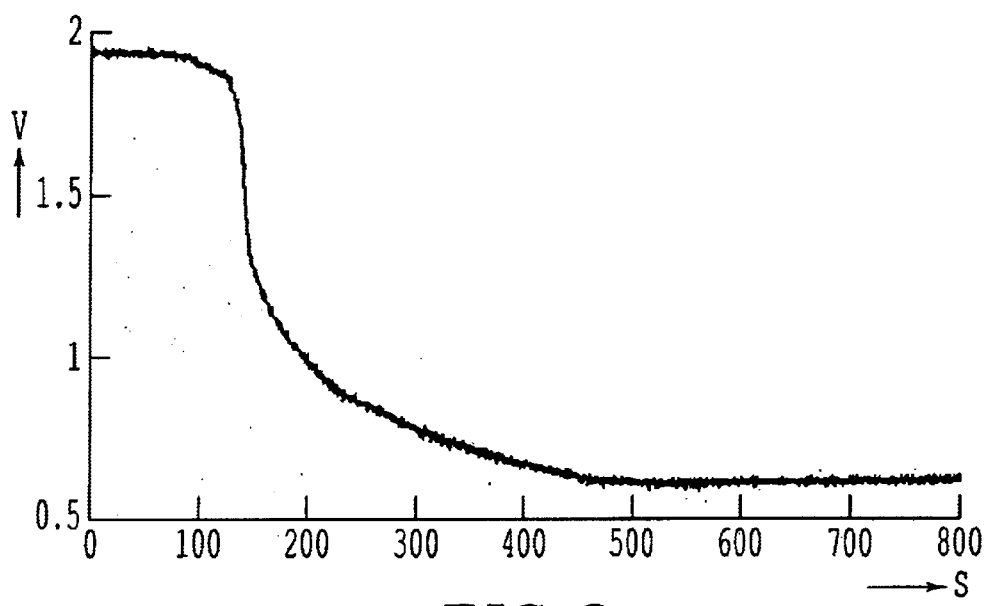
FIGS. 9 and 10 are graphs like FIGS. 3–6 showing the response of the apparatus of FIG. 8.

The sensor device was evaluated using the experimental set-up shown in FIG. 8. The large size of the device necessitated that evaluation was carried out in a much larger amount of sand 34 (500 g) than that used when testing prototypes. This, coupled with the inverted nature of the transducer, resulted in slow transportation of oil to the sensing head and therefore lengthened the response time of the sensor considerably. Typically oil added to the sand surface took between 15 and 30 minutes to reach the sensing membrane. The response observed when the oil reaches the sensor surface is shown in FIG. 9. Oil was added 15 minutes prior to the start of the plot.

Figure 10:
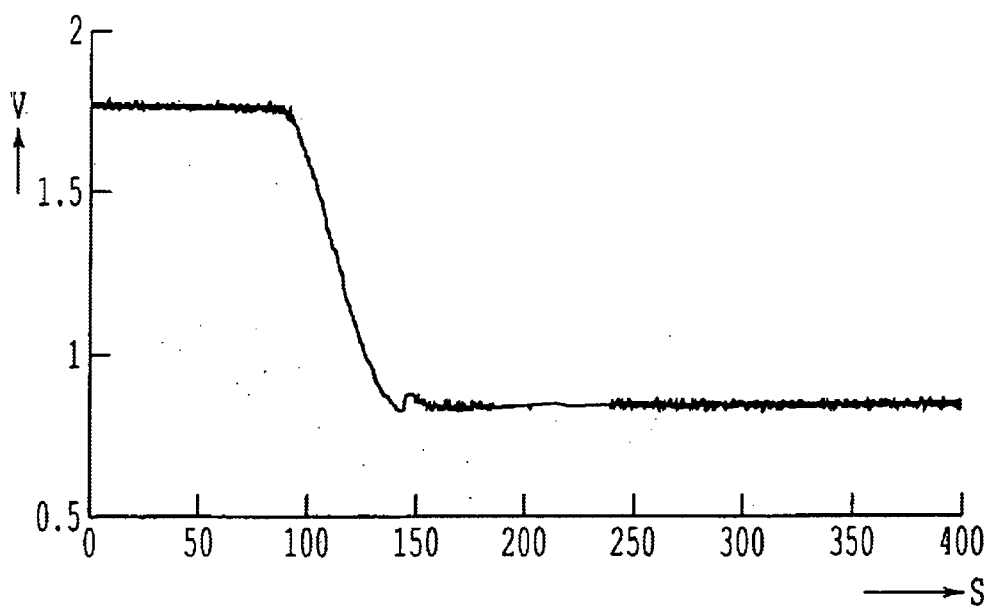

As a precautionary measure, it was decided that a protective mesh should be added in front of the sensing membrane to prevent the possibility of sand particles tearing the membrane when the transducer is being positioned. Due to the reflective nature of the mesh, the response to oil is slightly different (see FIG. 10; oil added 15 minutes prior to start of plot) but the distinction between the presence and absence of oil is still very clear.

1.3.1 Long Term Stability Tests

Additional tests were conducted to determine the integrity of the new sensor head in water and sand. These involved:

1. Leaving two transducers submerged in water for one month and checking that water did not enter the assembly or in any way affect the behaviour of the transducer.
2. Leaving two transducers buried in a beaker of sand containing 10% water for one month, then adding oil to check if the characteristic oil response was still observed.

In both cases both transducers passed without problems.

Identification of Different Hydrocarbons

Figure 11:
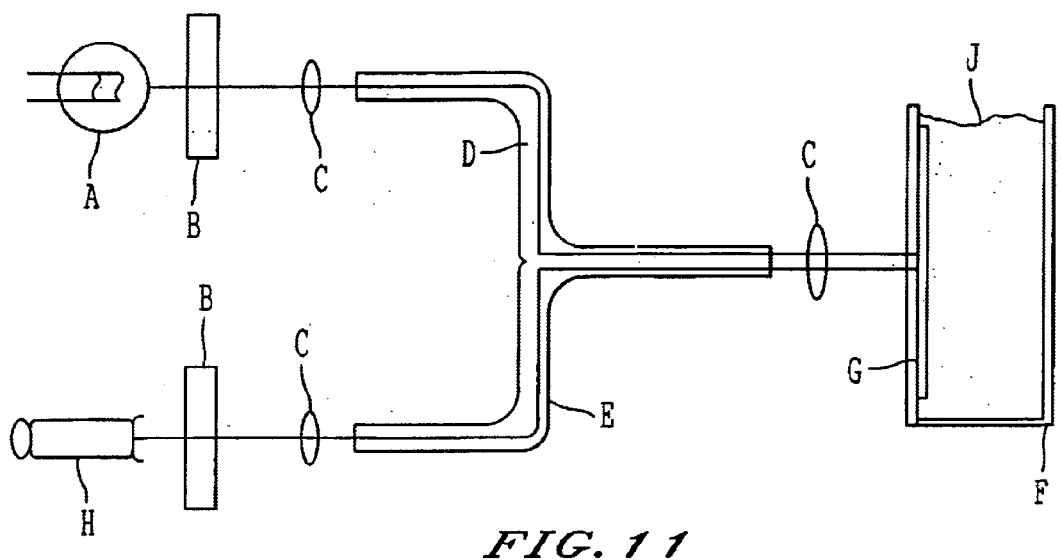
FIG. 11 is a schematic view of a second form of sensor assembly in use.

In order to demonstrate the detection of different types of hydrocarbon products, the sensor design was modified in order to measure the spectral characteristics of oils that were absorbed into the membrane from the environment. This was simulated in the laboratory by using a fibre optic configuration that illuminated the membrane in contact with soil and collecting the emitted light. In the presence of oil in the membrane, fluorescence emission occurs which is characteristic of each type of hydrocarbon material. The apparatus is shown in FIG. 11. The inner surface of a quartz cuvette F was lined with the fluoropolymer hydrophobic membrane G. The quartz-membrane interface represents the optical window design employed in the technical description above. The cuvette was packed with sand J to simulate the arrangement the optical-fibre sensor would take in the environment.

The optical fibre was connected to a spectrofluorimeter instrument H and synchronous scans of different fuel and oil samples were taken using the optical fibre collection system. The arrangement is shown in FIG. 11. The letters in this figure refer to the following: A=lamp, B=monochromator, C=focussing lens, D=excitation fibre, E=emission fibre, F=cuvette full of sand, G=membrane.

Figure 12A:
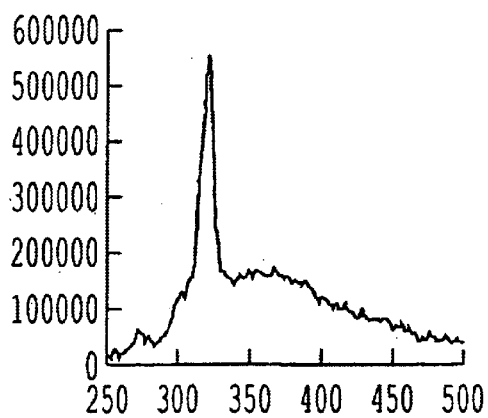
FIGS. 12A, B, C and D are fluorescence spectra produced using the assembly of FIG. 11.
Figure 12B:
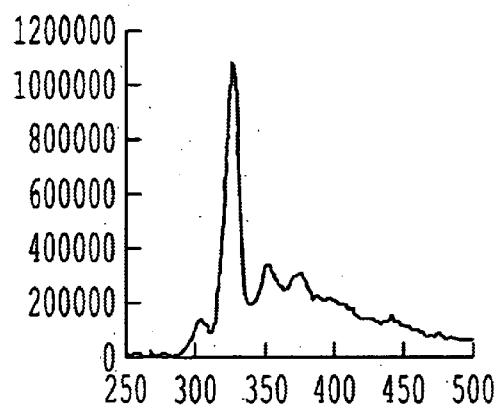
Figure 12C:
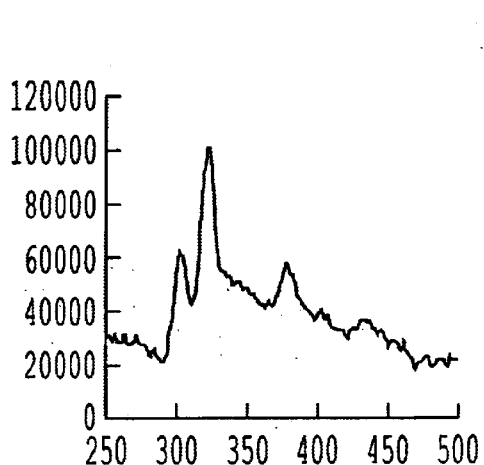
Figure 12D:
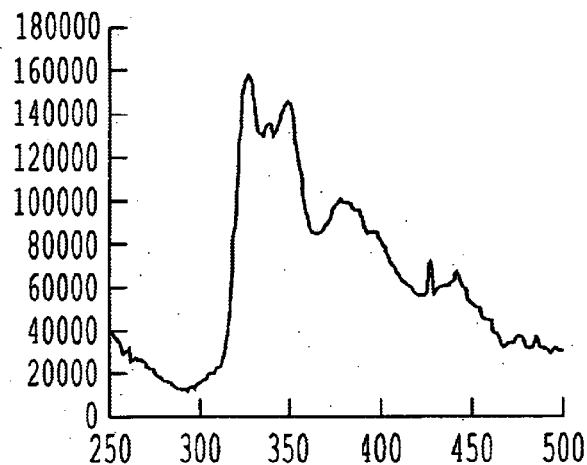

The fluorescence excitation beam was focussed onto the membrane using a quartz lens on the end of a 25-stranded quartz fibre-optic bundle. Fluorescence collection was facilitated by another 25-stranded group of fibres co-bundled with the excitation fibres. Synchronous scans were performed between 250 nm and 500 nm. FIG. 12 shows the fluoroescence spectra obtained from 4 different oil samples: cable oil (FIG. 12A), transformer oil (FIG. 12B), petrol (FIG. 12C) and diesel (FIG. 12D). This experimental evidence clearly shows the sensor can be used for the identification of different oils and other hydrocarbon liquids such as petroleum and diesel.

Figure 13:
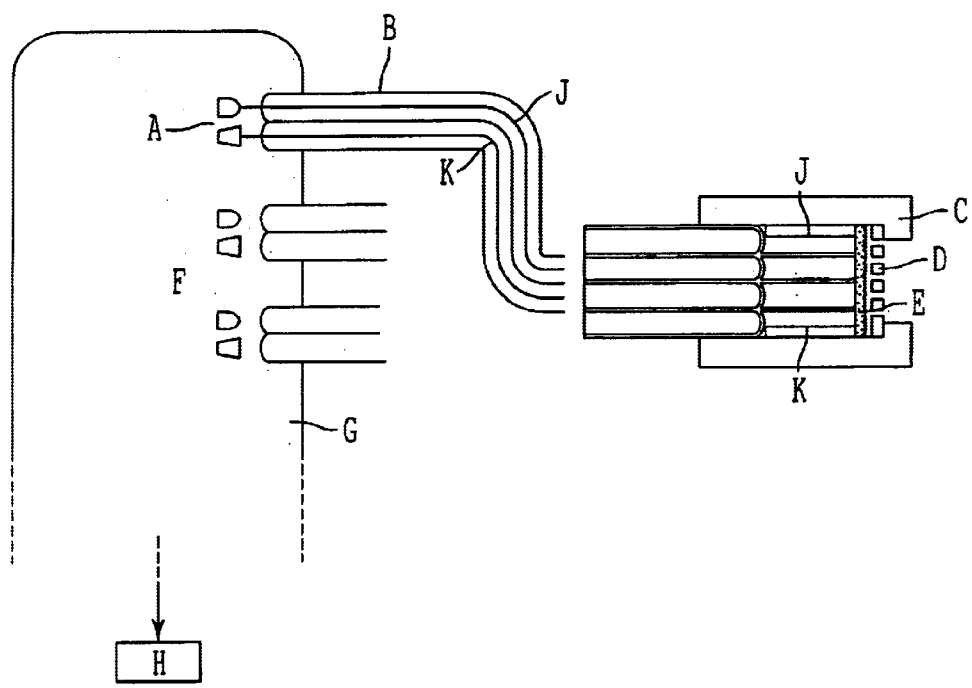
FIG. 13 is a schematic view of a multi-sensor device, with one sensor unit shown expanded.

FIG. 13 shows a multi-point fibre optic sensor using the same principle of detection. A multiplicity (e.g. 10) of sensors C are each connected to a common control unit G by a respective optical cable B containing two sets of fibres— one set for transmission of light to the membrane E, the other set K for collection of light reflected or emitted from the (liquid hydrocarbons on the) membrane. The transmission and collection fibres together are referred to as a pair.

Light is channelled down a transmission fibre optic bundle J which terminates in a sensor probe head C. The sensor head employs an identical membrane to that used previously, which is illuminated by the light from the transmission optical fibres. Light reflected from the membrane surface is collected by collection fibres K in the bundle and is delivered to a detector H.

When oil is present, the intensity of the reflected light diminishes or the spectroscopic properties of the emitted light is modified owing to the presence of liquid hydrocarbons. The length of the fibre optic pair can vary (typically 1–10 m in length).

A number of fibre optic pairs can be integrated by means of a single control device G. The device controls which fibre optic pair will be operated. Typically 1–10 pairs are used, and pairs may be of different length.

The control device is controlled by a microprocessor and can be controlled remotely using appropriate telecommunications.

What is claimed is:

1. A method of monitoring for the presence of hydrophobic liquid at a site comprising:

locating at said site a sensor assembly which comprises a polyvinylidene fluoride membrane which is adapted to take up hydrophobic liquid from the site, radiation input means connected to a radiation source and arranged to irradiate said membrane, and radiation output means connected to a radiation detector and/or analyser arranged to detect and/or analyse radiation which results from the irradiation of said membrane by said radiation input means;

causing the radiation input means to irradiate said membrane; and employing said detector/analyser to receive radiation via said radiation output means, the arrangement being such that the nature and/or amount of radiation received by the detector/analyser is affected by the presence of liquid at the site.

2. A method according to claim 1 wherein the radiation source and input means are operated to direct radiation towards said membrane and the detector/analyser and output means are used to receive radiation reflected from the membrane.

3. A method according to claim 1 wherein the radiation source and input means are operated to direct radiation towards said membrane and the detector/analyser and output means are used to receive radiation scattered from said membrane.

4. A method according to claim 1 wherein the radiation source and input means are operated to direct radiation towards said membrane and the detector/analyser and output means are used to receive radiation transmitted through said membrane.

5. A method according to claim 1 including a step of examining the spectroscopic characteristics of the radiation received by the detector/analyser to provide data relating to the chemical nature of liquid at the site.

6. A method according to claim 1 wherein the radiation source and the detector/analyser are remote from the site and are connected to the input and output means, respectively, via waveguide means.

7. A method according to claim 1 wherein there are a plurality of sensor assemblies which are located at different sites, and the method includes switching the connection of the radiation source and/or the detector/analyser between different sensor assemblies.

8. A sensor assembly for use in monitoring for the presence of hydrophobic liquid at a site, said assembly comprising:

a hydrophobic element comprising a polyvinylidene fluoride membrane which is disposed so that in use it is exposed to the environment at a sensing location and which is adapted to take up hydrophobic liquid; a radiation source arranged to irradiate at least a portion of the hydrophobic element; and a radiation detector and/or analyser arranged to receive radiation resulting from the interaction of the source's radiation with the hydrophobic element.

9. A sensor assembly according to claim 8 which includes a housing containing, or coupled to, said radiation source and said radiation detector and/or analyser; said housing having window means confronting said hydrophobic element; and said radiation source and detector/analyser being disposed or coupled so that radiation from the source can pass outwardly through the window means, and undergo reflection and/or other interaction at the hydrophobic element, interacted radiation passing inwardly through the window means to reach the detector analyser.

10. An assembly according to claim 6 wherein the detector/analyser comprises means for spectroscopic analysis.

11. An assembly according to claim 8 further comprising a vessel containing a hydrophobic liquid and wherein said hydrophobic element is located at a site potentially contaminated by liquid leaking from the vessel whereby said sensor assembly is operable to detect leakage of the liquid.

12. An assembly according to claim 8 adapted to carry out remote monitoring by means of a telecommunication link arranged to transfer data from the sensor assembly to a remote destination.

13. An assembly according to claim 8 wherein the radiation source and detector/analyser are adapted to be remote from the sensing location, being coupled to waveguide means for conveying radiation to and from the sensing location.

14. An assembly for carrying out the method of claim 7 and comprising a detector/analyser and/or a radiation source connected to a switching unit which is connected to a plurality of sensor assemblies and is operable to switch the connection of the radiation source and/or the detector/analyser between different sensor assemblies.

* * * * *